United States Patent
Martin

[11] 3,974,683
[45] Aug. 17, 1976

[54] ULTRASONIC APPARATUS FOR DETERMINING THE VOLUME OF BUBBLES IN LIQUID

[75] Inventor: Roger Martin, Reading, England

[73] Assignee: United Kingdom Atomic Energy Authority, England

[22] Filed: Sept. 13, 1974

[21] Appl. No.: 505,776

[30] Foreign Application Priority Data
Sept. 17, 1973 United Kingdom............... 43608/73

[52] U.S. Cl.............................. 73/432 PS; 73/61 R; 73/67.8 R
[51] Int. Cl.² ........................................ G01N 29/02
[58] Field of Search............ 73/67.7, 67.8 R, 67.8 S, 73/67.9, 61 R, 432 PS

[56] References Cited
UNITED STATES PATENTS

| | | | |
|---|---|---|---|
| 2,838,930 | 6/1958 | Krautkramer et al. | 73/67.8 |
| 3,033,029 | 5/1962 | Weighart | 73/67.8 R |
| 3,093,998 | 6/1963 | Albertson et al. | 73/61 R |
| 3,269,172 | 8/1966 | McGaughey | 73/61 R |
| 3,439,529 | 4/1969 | Patterson | 73/432 PS X |
| 3,710,615 | 1/1973 | Johnson et al. | 73/61 R |
| 3,802,271 | 4/1974 | Bertelson | 73/432 PS |

Primary Examiner—Richard C. Queisser
Assistant Examiner—John P. Beauchamp
Attorney, Agent, or Firm—Larson, Taylor and Hinds

[57] ABSTRACT

An apparatus for ultrasonic testing comprising a pulsed ultrasonic transducer, means for detecting echoes from bubbles in a liquid and means for determining the volume of the bubbles.

4 Claims, 1 Drawing Figure

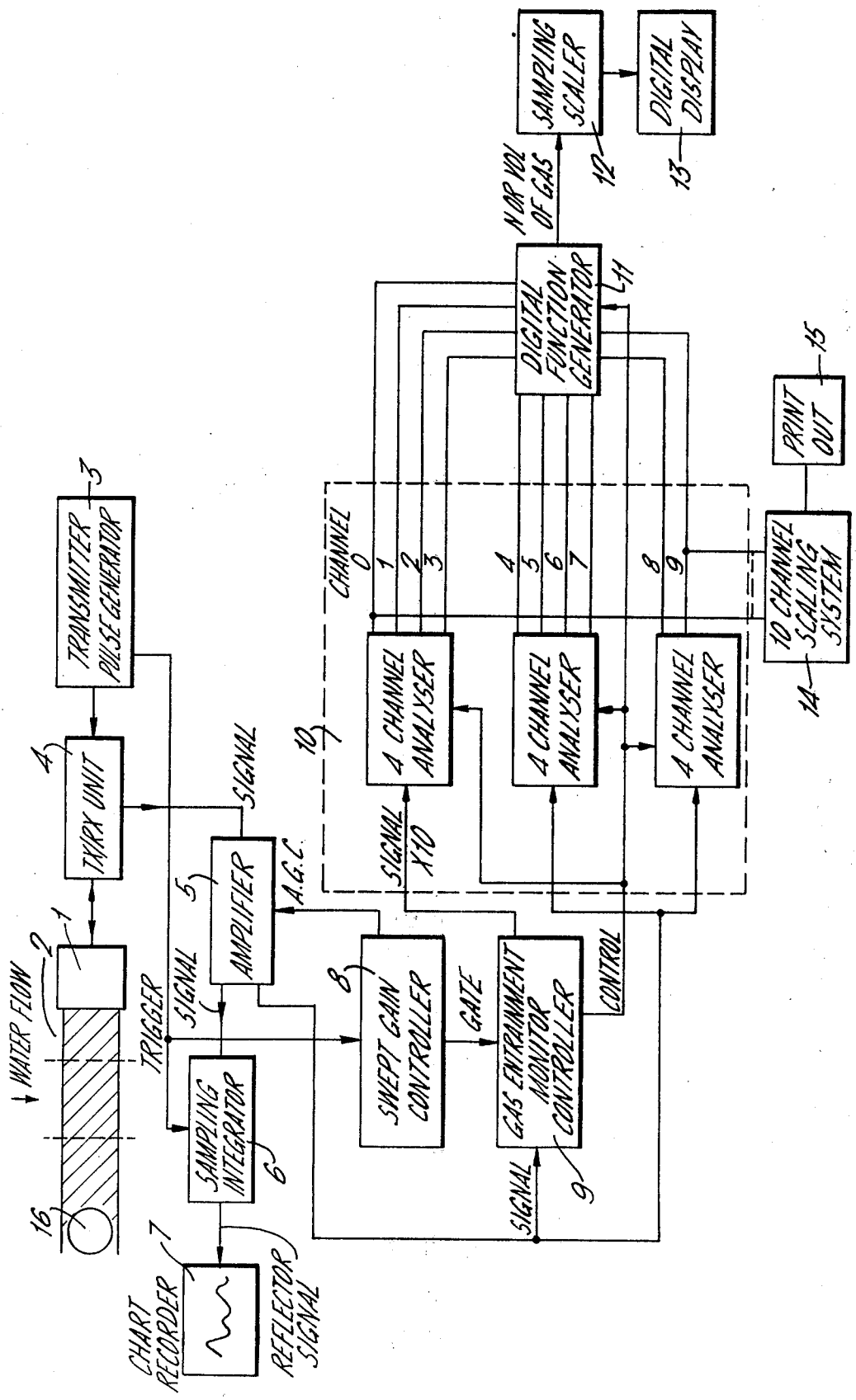

ULTRASONIC APPARATUS FOR DETERMINING THE VOLUME OF BUBBLES IN LIQUID

The present invention relates to ultrasonic testing, and more specifically to the measurement of the total volume of inclusions in a medium.

According to the present invention there is provided an apparatus for ultrasonic testing, including means for irradiating a medium under test with pulses of ultrasound, means for detecting echoes reflected from inclusions within the medium, and means for determining the total energy contained within the reflected pulses.

The amount of ultrasonic energy reflected by a bubble in a liquid medium, assuming that the bubble is small in cross-section in relation to the beam of ultra sound and at least comparable in size to the wavelength of the ultra sound used, will be a function of the square of the bubble radius, and also proportional to the inverse square of the distance of the bubble from the receiver of the ultra sound. Hence, in a particular embodiment of the invention — for determining the amount of gas entrained in a liquid, the detecting means includes an amplifier the gain of which varies as the square of the time which has elapsed since the time of emission of a pulse, and a non-linear element the output signal of which varies as the three halves power of the input signal to it.

An embodiment of the invention will be described, by way of example, with reference to the drawing accompanying the provisional specification which represents a block circuit diagram of a gas entrainment monitor.

Referring to the drawing, a gas entrainment monitor incorporating the invention consists of a piezo-electric crystal 1 which is acoustically coupled to a liquid medium 2, under test. The crystal 1 is connected to a pulse generator 3 via a transmitter/receiver unit 4 which enables it to function in a transmitting or a receiving mode. Any return signals received by the crystal 1 are passed by the unit 4 to a variable gain amplifier 5, and thence to a sampling integrator 6 and a chart recorder 7. The pulse generator 3 is also arranged to apply trigger pulses to the sampling integrator 6 to operate a gate contained therein, and to a gain control circuit 8 which varies the gain of the amplifier 5 according to a square law. The gain control circuit 8 also generates trigger pulses which are applied to another control circuit 9. The amplified return signals are also applied to the control circuit 9 and to a 10-channel signal analyser shown generally by the numeral 10. The four channel analyzers making up the signal analyzer 10 can, for example, comprise four tunnel diode discriminators whose thresholds are set to correspond to selected bubble sizes. The amplified return signals are applied directly to eight channels of the signal analyser 10 and to the other four channels via the control circuit 9. The outputs from the signal analyser 10 are applied to a digital function generator 11, which is arranged to produce an output signal which can be arranged to be representative either of the total number of gas bubbles present in the liquid, or of their total volume. This signal is fed to a sampling scaler 12 and a digital display unit 13. Alternatively the channel outputs from the signal analyser 10 are applied to a scaling system 14 and a print-out mechanism 15. Although they are not illustrated, facilities are provided to enable the position of the measurement and the duration of the sampling period to be varied. Provision also is made for the results of a number of samples to be averaged.

A reference reflector 16 is provided to give a standard signal for calibration purposes. It can also be used to enable a crude estimate of the void fraction of bubbles to be determined by measuring the attenuation of the beam of ultra sound.

It should be noted that the circuits shown in block form in the drawings are conventional off-the-shelf items and are included in a series of standard units of electronic equipment known as the Harwell 6000 series. Thus, transmit-receive unit 4 can be implemented by using Model No. 0457, transmitter pulse generator 3 by Model No. 0160, sampling integrator 6 by Model 8 by Model No. 0191, gas entrainment monitor controller by Model No. 71E/91, the 4 channel analyzers of unit 10 by Model No. 71E/78, the 10 channel scaling system 14 and printout 15 by Model No. 2612, the digital function generator 11 by Model No. 71E/72, sampling scaler 12 by Model No. 0175 and digital display 13 by Model No. 0450, all from the Harwell 6000 series referred to above.

The operation of the device is as follows:

The crystal 1 is shock excited by the pulse generator 3 to produce a short pulse of ultra sound which propagation through the water 2. Any bubbles in the water 2 scatter the ultra sound, and the back-scattered ultra sound is picked up by the crystal 1 when it is operating in the receiving mode. The velocity of propagation of the ultra sound is such that any distribution of bubbles can be considered to be constant for any given pulse of ultra sound. The received signal is amplified firstly by the transmitter/receiver unit 4, and then by the amplifier 5, which is tuned to the frequency of the crystal 1 to reduce noise effects. The time taken for each sweep of the swept gain control circuit 8 defines the active length of the ultrasonic beam over which the measurements of bubble size are made, and controls the gain of the amplifier 5 according to the square law which is necessary to ensure that the output signal from the amplifier 5 for a given bubble size is constant and independent of the bubble position along the axis of the beam of ultra sound. The amplified return signals from the amplifier 5 are applied to the operative channels of the signal analyzer 10 and enter the channel having the appropriate threshold level.

The control circuit 9 contains a threshold discriminator which produces a pulse each time the input signal to the control circuit 9 exceeds a value representative of a predetermined minimum bubble size. This pulse which appears on the output line labeled CONTROL is used to strobe, i.e., activate sequentially, the channels of the signal analyser 10 to determine into which one of the ten levels the input signal level fell. Thus, controller 9 determines whether the input signal exceeds a predetermined threshold while signal analyzer 10, upon being strobed by controller 9 when the threshold is exceeded, determines in which of ten levels the signal is properly classified. It is noted that controller 9 also includes an output line labeled SIGNAL X 10. This indicates that for channels 0–3 the input signal from amplifier 5 is amplified by a factor of 10 thus enabling the threshold levels for these channels to be set higher. The threshold levels of the channels of the signal analyser 10 follow a law such that the expected range of bubble size, say 0–2 mm, can be divided into 10 equal intervals.

As already described, the final signal can be processed in two ways; either the 10 channels of the signal analyser 10 can be fed into the digital function generator 11 which produces a number which is proportional to the void fraction or the outputs of the 10 channels of the signal analyser 10 can be recorded on the scaler 14 and print-out mechanism 15 to give a histogram of the distribution of bubble sizes. The digital function generator 11 contains a 16 bit binary storage register and whenever a signal occurs in one of the channels of the signal analyser 10 a number proportional to the volume of the mean bubble size in that channel is added into the binary register. To satisfy the second criterion, previously referred to, the number added is made to be a function of the cube of the respective channel number. This can be done in the signal analyzer 10 itself so that analyzer 10 corresponds to the non-linear element referred to above. When the signals corresponding to all the bubbles present in the water during a particular pulse of ultra sound have been accumulated, a conversion is carried out to allow for the volume of water which has been sampled, and a number representative of the void fraction is fed to the scaler 12 and the display unit 13.

The sampling integrator 6 includes a gate, which is operated by the trigger pulses, and so operates that the output signal produced by the sampling integrator 6 is proportional to the amplitude of the signal received from the reflector 16. At high void fractions when a saturation effect occurs in the remainder of the system, the amplitude of the reflected signal can be used as a measure of the void fraction.

At high void fractions, bubble pile-up could cause errors. The signal received from the reflector 16 could be used in a feed-back system to vary the gain of the amplifier 5 to compensate for such errors.

We claim:

1. Apparatus for measuring the gaseous content of bubbles entrained in a liquid, comprising means for irradiating a liquid under test with pulses of ultra sound having a wavelength comparable in size with the bubbles, means for detecting echo signals from the bubbles, an amplifier for amplifying the echo signals, means for varying the gain of the amplifier as a function of the time which elapses subsequent to the emission of a given pulse of ultra sound, means for producing output signals proportional to the amplified signals raised to the power of three halves, and means responsive to the output signals to provide an indication of the gaseous content of the bubbles.

2. Apparatus according to claim 1 wherein the means for producing an indication of the gaseous content of the bubbles comprises means for producing an indication of the volume fraction of bubbles in the liquid.

3. Apparatus according to claim 1 wherein the means for producing an indication of the gaseous content of the liquid comprises means for producing an indication of the total volume of bubbles in the liquid.

4. Apparatus according to claim 1 wherein the means for producing an indication of the gaseous content of the liquid comprises means for producing a histogram showing the distribution of the bubble sizes.

* * * * *